US008668944B2

(12) United States Patent
Greco

(10) Patent No.: US 8,668,944 B2
(45) Date of Patent: Mar. 11, 2014

(54) TOPICAL OIL FOR TREATING PHYSICAL AILMENTS AND METHOD FOR MAKING AND APPLYING THE SAME

(76) Inventor: Donna Greco, Saugerties, NY (US)

( * ) Notice: Subject to any disclaimer, the term of this patent is extended or adjusted under 35 U.S.C. 154(b) by 635 days.

(21) Appl. No.: 11/695,653

(22) Filed: Apr. 3, 2007

(65) Prior Publication Data

US 2008/0248138 A1  Oct. 9, 2008

(51) Int. Cl.
*A61K 8/97* (2006.01)
*A61K 36/185* (2006.01)
*A61K 36/736* (2006.01)
*A61K 36/00* (2006.01)

(52) U.S. Cl.
USPC ........... 424/765; 424/735; 424/776; 424/779; 424/725

(58) Field of Classification Search
None
See application file for complete search history.

(56) References Cited

U.S. PATENT DOCUMENTS

| 5,288,491 | A | 2/1994 | Moniz |
| 6,214,351 | B1 | 4/2001 | Wadsworth et al. |
| 6,436,449 | B2 | 8/2002 | Gidlund |
| 6,544,530 | B1 | 4/2003 | Friedman |
| 6,589,514 | B2 | 7/2003 | Jensen et al. |
| 7,018,662 | B2 | 3/2006 | Jensen et al. |
| 2002/0187168 | A1 | 12/2002 | Jensen et al. |
| 2002/0192245 | A1 | 12/2002 | Jensen et al. |
| 2002/0192246 | A1 | 12/2002 | Jensen et al. |
| 2003/0086989 | A1 | 5/2003 | Jensen et al. |
| 2003/0091666 | A1 | 5/2003 | Murad et al. |
| 2003/0161901 | A1 | 8/2003 | West et al. |
| 2005/0196476 | A1 | 9/2005 | Zhou et al. |
| 2006/0159788 | A1 | 7/2006 | West et al. |

FOREIGN PATENT DOCUMENTS

JP    2001-213758 A * 8/2001 ............... A61K 7/50

OTHER PUBLICATIONS

"Goodnoni Moisturizing Cream". Internet Archive Date: Jul. 27, 2005 [Retrieved from the Internet on: Jun. 17, 2009]. Retrieved from: <http://web.archive.org/web//http://www.goodnoni.biz/>.*
"Alba Jasmine & Vitamin E Moisture Cream". Internet Archive date: Nov. 4, 2006 [Retrieved from the Internet on: Jun. 17, 2009]. Retrieved from: <http://web.archive.org/web//http://www.albaorganics.com/?id=55&pid=330>.*
Almond (sweet) oil. Retrieved from the internet. <http://web.archive.org/web/20041122214033/http://www.aromaland.com/shop/index.cfm?fuseaction=customer.product&product_code=71ALM8>. web archive date 2004. Retrieved on May 18, 2010.*
Zin et al. Antioxidative Activity of Extracts From Mengkudu (*Morinda citrifolia* L.) Root, Fruit and Leaf. Food Chemistry. 78 (2002). 227-231.*
Green. The Herbal Medicine-Maker's Handbook: A Home Manual. Random House Digital, Inc. 2000. p. 198.*
Jones. The Antibiotic Alternative: The natural guide to fighting infection and maintaining a healthy immune system. Inner Traditions/Bear & co. 2000. p. 208.*

* cited by examiner

*Primary Examiner* — Chris R Tate
*Assistant Examiner* — Deborah Davis
(74) *Attorney, Agent, or Firm* — Schmeiser, Olsen & Watts, LLP

(57) ABSTRACT

A method for making and applying a topical oil and composition thereof, combining the healing properties of the Noni plant with a topical application for treating physical ailments. The topical oil disclosed includes an oil derived from raw leaves, stems, and buds of a noni plant; a carrier oil; and vitamin E oil.

8 Claims, No Drawings

TOPICAL OIL FOR TREATING PHYSICAL AILMENTS AND METHOD FOR MAKING AND APPLYING THE SAME

BACKGROUND OF THE INVENTION

1. Field of the Invention

The present invention relates to a method of making and applying a topical massage oil and composition thereof, and more particularly, to a composition and method of making and applying oil utilizing an infusion process to extract potent ingredients from the Indian Mulberry plant (hereinafter referred to as "Noni plant") for treating physical ailments.

2. Description of the Related Art

U.S. Patent Application 20020192246 to Jensen, et al. discloses an intensive repair serum formulated with *Morinda Citrifolia*, or Noni, also known as the Indian Mulberry plant.

U.S. Patent Application 20020192245 to Jensen, et al. discloses a night creme formulated with *Morinda Citrifolia*, or Noni, from the Indian Mulberry plant.

U.S. Patent Application 20020187168 to Jensen, et al. discloses a toner formulated with *Morinda Citrifolia*, or Noni, from the Indian Mulberry plant.

U.S. Patent Application 20060159788 to West, et al. discloses a novel use of one or more processed *Morinda citrifolia*-based naturaceutical formulations comprising one or more of a processed *Morinda citrifolia* fruit juice, puree juice, oil or oil extract, dietary fiber, alcohol extract, etc., for inhibiting and preventing the overgrowth of *Candida* fungus and for treating Candidiasis and its associated symptoms.

U.S. Patent Application 20030091666 to Murad discloses methods and pharmaceutical compositions for treating dermatological disorders. The methods include administering a therapeutically effective amount of an extract of *Morinda citrifolia*. The compositions include an extract of *Morinda citrifolia*; and at least one of a moisturizing agent in an amount sufficient to facilitate hydration of the skin or hydrogen peroxide in an amount sufficient to cleanse at least a portion of the skin.

U.S. Patent Application 20030086989 to Jensen, et al. discloses a lip treatment formulated with *Morinda citrifolia* juice or oil.

U.S. Patent Application 20050196476 to Zhou, et al. discloses methods and compositions relating to leaf extracts obtained from removing liquids from relatively dry *Morinda citrifolia* leaves. Methods and compositions relating to a leaf serum created from combining leaf extract and fruit juice from the *Morinda citrifolia* L. plant.

U.S. Patent Application 20030161901 to West, et al. discloses a novel use of processed ingredients from the Indian mulberry plant, and particularly a novel use of one or more processed *Morinda citrifolia*-based naturaceutical formulations comprising one or more of a processed *Morinda citrifolia* fruit juice, puree juice, oil or oil extract, dietary fiber, alcohol extract, etc., for inhibiting and preventing the overgrowth of *Candida* fungus and for treating Candidiasis and its associated symptoms.

U.S. Pat. No. 6,589,514 to Jensen, et al. discloses an intensive repair serum formulated with *Morinda citrifolia* from the Indian Mulberry plant.

U.S. Pat. No. 6,214,351 to Wadsworth, et al. discloses an essential oil product obtained from the Indian mulberry (*Morinda citrifolia*) plant and the process of extracting and purifying the oil is disclosed. According to one embodiment, the seeds from the Indian mulberry fruit are dried, preferably to a moisture content less than 10%. The seeds are ground or shredded to facilitate the removal of natural occurring oil. The shredded or ground flakes are pressed to expel *Morinda citrifolia* oil. The remaining seed cake is then mixed with a food grade, non-polar extraction solvent such as hexane. The mixture is heated for a sufficient length of time to complete the extraction process. The extraction solvent is then evaporated from the mixture leaving the *Morinda citrifolia* oil. The oil is further refined, bleached, dried, and deodorized to remove free fatty acids and other unwanted components. An antioxidant can optionally be added to stabilize the oil for further processing or packaging.

U.S. Pat. No. 6,436,449 to Gidlund discloses use of an extract derived from the fruits, leaves, the bark or the roots of *Morinda citrifolia* L. for the manufacture of a medicament for the treatment of a mammal suffering from tinnitus. The extract may be a liquid present in the medicament in an amount such as to give a daily dosage of 0.1-2 ml, or 0.2-1 ml, e.g. 0.4-0.7 ml, per kg body weight of the patient. The extract also may be a solid present in the medicament in an amount such as to give a daily dosage of 5-200 mg, or 10-100 mg, e.g. 20-70 mg, per kg body weight of the patient. Optionally, the medicament also may comprise lycopene, vitamine C, coenzyme Q10 and an extract from the leaves of *Ginkgo biloba*. The medicament may be given e.g. by oral, rectal, transdermal or inhalation administration.

U.S. Pat. No. 6,544,530 to Friedman discloses a composition of matter comprising a stable oil-in-glycerin emulsion containing at least one oil, at least one emulsifier and glycerin.

U.S. Pat. No. 7,018,662 to Jensen, et al. discloses a method of preventing and treating various ailments and diseases by using the Cox-2 selective inhibition characteristics of processed *Morinda Citrifolia*.

U.S. Pat. No. 5,288,491 to Moniz discloses a method for processing the noni plant into powder. The method for processing the noni plant into powder, includes the steps of picking the noni fruit from the tree, placing picked noni fruit in a room, washing and cleaning the noni plant, mashing the noni fruit, placing the pulp onto liner, rotating trays for five hours, rotating trays for another five hours, rotating trays for another 14 hours, and crushing and grinding dried wafers.

While these units may be suitable for the particular purpose employed, or for general use, they would not be as suitable for the purposes of the present invention as disclosed hereafter.

SUMMARY OF THE INVENTION

The Noni plant is commonly a shrub, or a small to medium sized tree. The Noni plant grows in tropical coastal regions around the world and is known to grow randomly in the wild, as well as being cultivated on plantations.

The Noni plant contains small white flowers which develop into compound fruits that are composed of many small drupes. The fruit may be juicy or bitter and contains numerous (2)-celled stones, each having (4) seeds.

Recently, there has been an interest in the nutritional and health benefits of the Noni plant. Modern researchers are striving to find answers as to why the Noni plant is able to alleviate many different kinds of physical ailments.

The present invention in a first aspect is topical massage oil comprising, in combination: oil derived from pulp of a Noni plant; a carrier oil; and vitamin E oil.

In a second aspect, A method for making a topical oil, comprising one pound of a raw Noni plant, including the leaves, stems, buds, pure organic oil, and four ounces of vitamin E oil, the steps comprising: providing a raw Noni plant, including the leaves, stems, buds and pure carrier oil; chopping the leaves, stems, and buds of the Noni plant; crushing the leaves, stems, buds of the Noni plant into a pulp;

combining the pulp of the Noni plant with the carrier oil; heating the oil; maintaining the oil at the temperature of at least about 145 to 165 degrees Fahrenheit for about thirty minutes; cooling the oil slowly; storing the oil in a container; infusing the leaves, stems, buds in the oil for up to three months; and filtering the pulp from the oil.

A third aspect of the present invention is a method for applying Noni oil, the steps comprising: washing the affected area; applying the Noni oil to the affected area; and rubbing the Noni oil into the affected area.

DETAILED DESCRIPTION OF THE INVENTION

The present invention is a method for making and applying Noni oil and composition thereof (hereinafter referred to as "Noni oil"). In its broadest sense, the method combines carrier oil, such as sweet almond oil, vitamin E oil, and crushed leaves, stems, and buds from the Noni plant.

The composition comprises one pound of raw Noni plant per one gallon of carrier oil such as any pure, organic oil. Carrier oil, such as base oil or vegetable oil, is used to dilute Noni oil before it is applied to the skin. It "carries" the essential Noni oil onto the skin. The advantage of the carrier oil is that it does not evaporate like the essential or Noni oil providing a longer time by which the oil is useable both in application and storage. Additionally, during the manufacture, the Noni oil is stored for up to 3 months and may be susceptible to evaporation. Thus, the carrier oil prevents more Noni oil during manufacture from evaporating.

The carrier oil may be either sweet almond oil, or grapeseed oil. Other acceptable carrier oils include avocado oil, olive oil, sesame oil, evening primrose, sunflower oil, kukui nut oil, jojoba oil, walnut oil, peanut oil, pecan oil, *macadamia* nut oil, and fractionated coconut oil. The carrier oil may also be combinations of the aforementioned carrier oils.

In addition to the carrier oil, approximately one to four ounces of vitamin E oil may be used per gallon of carrier oil. In many cases one ounce of carrier vitamin E oil is used. Vitamin E oil or tocopherol is a biological antioxidant. As an antioxidant, it protects cells against the effects of free radicals. Free radicals may be damaging to the by-products of the body's metabolism and may contribute to the development of cardiovascular disease and cancer. Additionally, studies of vitamin E suggest it is useful in preventing cataracts, age related macular degeneration, Alzheimer's disease and Parkinson's disease. Vitamin E oil is a natural preservative, helping stabilize the oil. The anti-oxidant properties of vitamin E will protect the oil from spoilage thereby increasing the shelf life of the finished product.

The method of making the Noni oil involves combining raw Noni plant leaves, stems, and buds, which are crushed and chopped into a pulp. Next, carrier oil such as organic oils are added to the pulp. The mixture of carrier oil and pulp is then heated to about 145 to 165 degrees Fahrenheit and the temperature is maintained for about thirty minutes to forty minutes. The mixture of oil and pulp is slowly cooled and stored preferably in large plastic drums, while the oil infuses for one to three months. Vitamin E is added during the cooling process. The mixture of oil and pulp is preferably stored at a temperature of between about sixty and eighty degrees Fahrenheit during the infusion process. The infusion process includes a method of extracting potent ingredients from the Noni plant by steeping the leaves, stems, and buds over time. This process also naturally extracts the color and scent from the noni plant into the carrier oil. The pulp from the crushed Noni plant leaves, stems, and buds is strained and pumped through a filter to extract the oil.

The Noni oil is a clear natural green colored oil with a low viscosity. Noni oil is derived from, *Morinda Citrifolia*, commonly known as Great *Morinda* or Indian Mulberry. The Indian Mulberry is a shrub or small tree in the family Rubiaceae. *Morinda Citrifolia*, which originated in Southeast Asia but may be found throughout India, the Pacific islands, and the West Indies.

The Noni plant flowers and fruits all year round. The flowers from the Noni plant are small and white. The fruit is oval shaped and reaches 4-7 cm in size. When ripening, the fruit is green, then yellow, then almost white as it ripens. It contains many seeds.

The oil from the Noni is abundant in linoleic acid or cis, cis-9,12-octadecadienoic acid. Linoleic acid is an unsaturated omega-6 fatty acid. It is a carboxylic acid with an 18-carbon chain and two cis double bonds; the first double bond is located at the sixth carbon from the omega end having a structure of $CH_3-(CH_2)_4-(CH=CH-CH_2)_2-(CH_2)_6-COOH$. Linoleic acid may be found in the lipids of cell membranes. The body processes Linoleic acid by converting it into gamma-linolenic acid. The enzyme delta-6-desaturase (D6D) catalyzes the reaction.

Linoleic acid is an omega-6 fatty acid essential for humans diets. The omega-3 fatty acids are also essential for human diets, for example Alpha-linolenic acid. Omega-6 deficiency symptoms manifest themselves in dry hair, hair loss, and poor wound healing.

The Noni oil takes on a natural scent of the Noni plant, which is slightly herbal and earthy. The Noni oil uses a topical application for treating physical ailments. Possible treatments include, but are not limited to, muscle pain, joint pain and arthritis, inflammation, and skin irritations. Some other characteristics of Noni oil include, but not limited to anti-inflammatory, anti-histamine, anti-bacterial and anti-fungal properties. It controls infectious bacteria, helps cell rejuvenation, is an anti-oxidant and contains essential amino acids.

Other uses of Noni include acne reduction, skin moisture retention, treatment for respiratory difficulties, infection, menstrual cramps, broken bones, toothache, gingivitis, urinary difficulties, and a shampoo for head lice. Scientific studies have also investigated noni's effect on the inhibition and growth of cancer.

In one method of the present invention, sweet almond oil to grapeseed oil is provided in a ratio of 3:1 (3 parts sweet almond to 1 part grapeseed oil, or a range of about between 20-30% grapeseed oil to about 70-80% sweet almond oil, or more particularly the carrier oil may be 25% grapeseed oil to 75% sweet almond oil. The vitamin E oil is added during the cooling process at a rate of 1 oz per gallon or 0.015% vitamin E to 98.985% carrier oil, or in a range of about between 0.010-0.020% vitamin E to 99.98-99.99% carrier oil. The noni pulp is added at about one pound (dry weight) per one gallon liquid oil.

The present invention in use involves a method of applying the Noni oil to an ailment. This can include, but is not limited to skin irritations muscle and joint pain, minor wounds and inflammation. The method involves washing a user's affected area and then applying, preferably several drops of the Noni oil to the affected area. Preferably, a dropper is used to apply the Noni oil to avoid contamination and excess waste. The user then preferably rubs the Noni oil into the skin of the affected area. The user may selectively cover the affected area. Lastly, the user may reapply the Noni oil when symptoms persist and stop if symptoms worsen.

In conclusion, herein is presented a method for making Noni oil and composition thereof, combining the healing properties of the Noni plant with a topical application for treating physical ailments. The invention is illustrated by example throughout the written description. It should be understood that numerous variations are possible, while adhering to the inventive concept. Such variations are contemplated as being a part of the present invention.

What is claimed is:

1. A topical oil comprising:
   an oil derived from pulp of at least one of the leaves, stem and buds of a noni plant;
   a sweet almond carrier oil; and
   vitamin E oil;
   wherein the oil derived from the pulp of at least one of the leaves, stems and buds of the noni plant is infused into the sweet almond carrier oil.

2. A topical oil prepared by the process comprising the steps of:
   providing a sweet almond carrier oil;
   providing at least one of the leaves, stem and buds of a noni plant;
   providing a vitamin E oil;
   combining the at least one of the leaves, stems and buds of the noni plant with the sweet almond carrier oil and the vitamin E oil into the topical oil;
   heating the topical oil; and
   infusing the at least one of the leaves stems and buds of the noni plant into the carrier oil.

3. The topical oil of claim 2, further prepared by the process comprising the step of filtering out the at least one of the leaves stems and buds of the noni plant from the topical oil.

4. The topical oil of claim 2, further prepared by the process comprising the step of maintaining the oil at the temperature between 145 to 165 degrees Fahrenheit for at least thirty minutes.

5. The topical oil of claim 2, further prepared by the process comprising the step of storing the oil in a container.

6. The topical oil of claim 2, further prepared by the process comprising the step of infusing the leaves, stems, buds in the oil for up to three months.

7. The topical oil of claim 2, wherein the topical oil is stored at between sixty and eighty degrees Fahrenheit.

8. The topical oil of claim 2, wherein vitamin E oil is added after the step of cooling slowly.

* * * * *